(12) United States Patent
Van Dalen

(10) Patent No.: US 9,032,962 B2
(45) Date of Patent: May 19, 2015

(54) APPARATUS, COMPOSITION, AND METHOD TO TREAT AMBLYOPIA

(76) Inventor: Johan T. W. Van Dalen, Tucson, AZ (US)

( * ) Notice: Subject to any disclaimer, the term of this patent is extended or adjusted under 35 U.S.C. 154(b) by 562 days.

(21) Appl. No.: 13/253,765

(22) Filed: Oct. 5, 2011

(65) Prior Publication Data

US 2012/0123313 A1    May 17, 2012

Related U.S. Application Data

(60) Provisional application No. 61/390,077, filed on Oct. 5, 2010.

(51) Int. Cl.

| | |
|---|---|
| *A61F 9/00* | (2006.01) |
| *A61B 3/00* | (2006.01) |
| *A61H 5/00* | (2006.01) |
| *A61F 9/04* | (2006.01) |
| *A61F 13/12* | (2006.01) |
| *G02C 5/00* | (2006.01) |
| *G02C 7/10* | (2006.01) |

(52) U.S. Cl.
CPC .................. *A61F 9/04* (2013.01); *A61F 13/124* (2013.01); *A61B 3/00* (2013.01); *G02C 5/001* (2013.01); *G02C 7/104* (2013.01); *A61H 5/00* (2013.01)

(58) Field of Classification Search
CPC ........... A61F 9/04; A61F 13/124; G02C 7/02; G02C 7/10; G02C 7/104; A61B 3/00; A61H 5/00
USPC ............ 128/857, 858; 351/46, 158, 200, 203, 351/246; 601/37; 606/4; 2/15; 320/101, 320/114, 115, 136
See application file for complete search history.

(56) References Cited

U.S. PATENT DOCUMENTS

| | | | |
|---|---|---|---|
| 7,452,067 B2 * | 11/2008 | Gross | 351/45 |
| 2002/0140899 A1 * | 10/2002 | Blum et al. | 351/159 |
| 2007/0030442 A1 * | 2/2007 | Howell et al. | 351/158 |

* cited by examiner

*Primary Examiner* — Alireza Nia
*Assistant Examiner* — Keri J Nelson
(74) *Attorney, Agent, or Firm* — Dale F. Regelman; Quarles & Brady LLP

(57) ABSTRACT

An ophthalmological device, comprising an eye patch, a photovoltaic, and a battery, wherein said photovoltaic is interconnected to said battery.

9 Claims, 12 Drawing Sheets

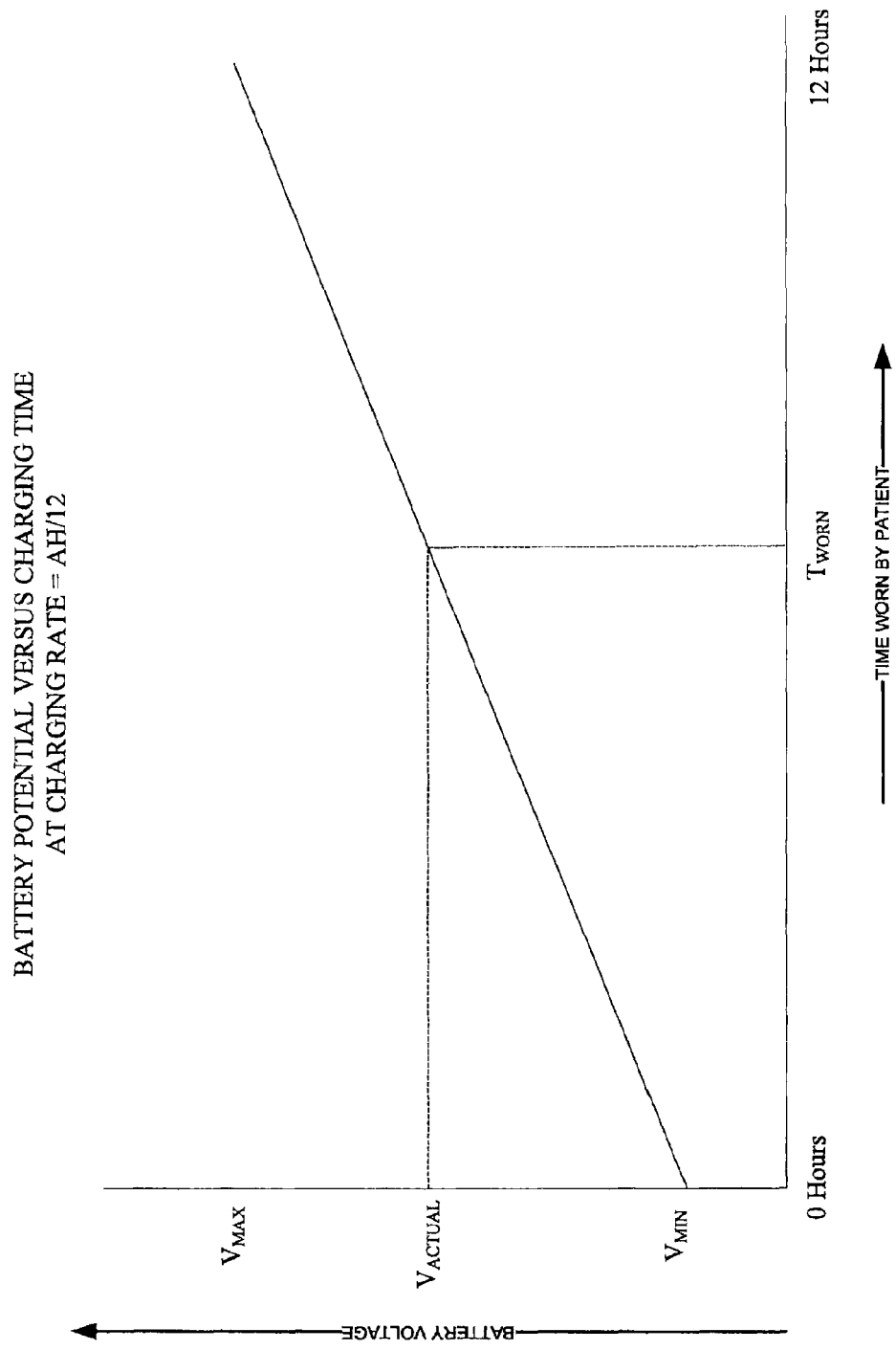

APPARATUS, COMPOSITION, AND METHOD TO TREAT AMBLYOPIA

CROSS-REFERENCE TO RELATED APPLICATIONS

This application claims priority from a U.S. Provisional Application filed Oct. 5, 2010 having Ser. No. 61/390,077.

FIELD OF THE INVENTION

The invention relates to an ophthalmological device, and a method to treat amblyopia using that device.

BACKGROUND OF THE INVENTION

Amblyopia, commonly known as lazy eye, is the eye condition noted by reduced vision not correctable by glasses or contact lenses and is not due to any eye disease. The brain, for some reason, does not fully acknowledge the images seen by the amblyopic eye. This almost always affects only one eye but may manifest with reduction of vision in both eyes. It is estimated that three percent of children under six have some form of amblyopia.

Both eyes must receive clear images during the so-called critical period, i.e. between birth to 6 years of age. Anything that interferes with clear vision in either eye during this critical period can result in amblyopia, i.e. a reduction in vision not corrected by glasses or elimination of an eye turn. The most common causes of amblyopia are constant strabismus (constant turn of one eye), anisometropia (different prescriptions in each eye), and/or blockage of an eye due to trauma, lid droop, etc. If one eye sees clearly and the other sees a blur, the good eye will inhibit (block, suppress, ignore) the eye with a blur. Thus, amblyopia is a neurologically active process. This inhibition results in a permanent decrease in the vision in that eye that is not corrected just with glasses.

Because amblyopia usually occurs in one eye only, many children may be unaware of the condition. As far too many parents fail to take their infants and toddlers in for an early comprehensive vision examination, many children go undiagnosed until they have their eyes examined at the eye doctor's office at a later age. The most important diagnostic tools are the special visual acuity tests other than the standard letter charts used by the eye doctor. Examination with cycloplegic drops can be necessary to detect this condition in the young.

If not detected and treated early in life, amblyopia can cause a permanent loss of vision with associated loss of stereopsis (two eyed depth perception). Detection and correction before the age of two offers the best chance for restoration of normal vision. Amblyopia can be treated fairly successfully between the ages of 2 and 6, but the success decreases with age. The best results from treatment occurs between ages 6 months. to 2 years.

Eye patches have long been a standard treatment for amblyopia. Typically, an ophthalmologist prescribes covering the "strong" eye with the eye patch for several hours during the day when the patient is constantly using his/her eyes. By covering the "strong" eye, the "lazy" eye is forced into service. Forced use of the "lazy" eye tends to strengthen that eye, and thus ameliorate the symptoms of amblyopia.

Children and parents alike, however, sometimes have difficulty following through. Even if the child is initially enthusiastic about looking like a pirate, consistently wearing an eye patch for a prescribed time period each day for days, weeks, or months, can become burdensome leading to non-compliance.

When a patient returns to the ophthalmologist for follow-up care, the physician would like to know, with some degree of accuracy, how long the patient actually wore the eye patch in the intervening time period since the previous examination. For example, if the patient reports wearing the eye patch for 5 hours daily for thirty days, and the physician does not observe the hoped-for improvement in the "lazy eye," then the physician might ask the patient to wear the eye patch for more hours each day. On the other hand, if the patient reports that he/she did not diligently follow the 5 hour per day treatment regime, then the physician might not increase the daily patch interval. Rather, the physician might counsel the patient about the necessity to follow through with the prescribed treatment protocol. Patient averments, and/or the averments made by the parents of the patient, regarding how long the patient actually wore the patch each day are typically inaccurate.

SUMMARY OF THE INVENTION

Applicant's invention comprises an ophthalmological device that indicates how long an eye patch was worn on a daily basis. In certain embodiments, Applicants' ophthalmological device comprises an eye patch, a photovoltaic, and a battery, wherein Applicants' method measures and uses a battery potential to determine a length of time the eye patch was worn. In certain embodiments, Applicants' eye patch comprises a photovoltaic and an oscillator comprising a counter, wherein Applicants' method reads a count value each day, and determines a length of time the eye patch was worn.

BRIEF DESCRIPTION OF THE DRAWINGS

The invention will be better understood from a reading of the following detailed description taken in conjunction with the drawings in which like reference designators are used to designate like elements, and in which:

FIG. 5B graphically illustrates a time worn by a patient versus a measured battery potential.

DETAILED DESCRIPTION OF THE PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In various embodiments, Applicants' ophthalmological device can measure, on a daily basis, the time a patient actually wears the ophthalmological device. In the illustrated embodiments of FIGS. 1A and 1C, Applicants' ophthalmological device comprises an eye patch, a battery and a photodiode. An eye patch or eye pad is a small patch that is worn in front of one eye. It may be a cloth patch attached around the head by an elastic band or by a string, or an adhesive bandage.

Figure 1A:
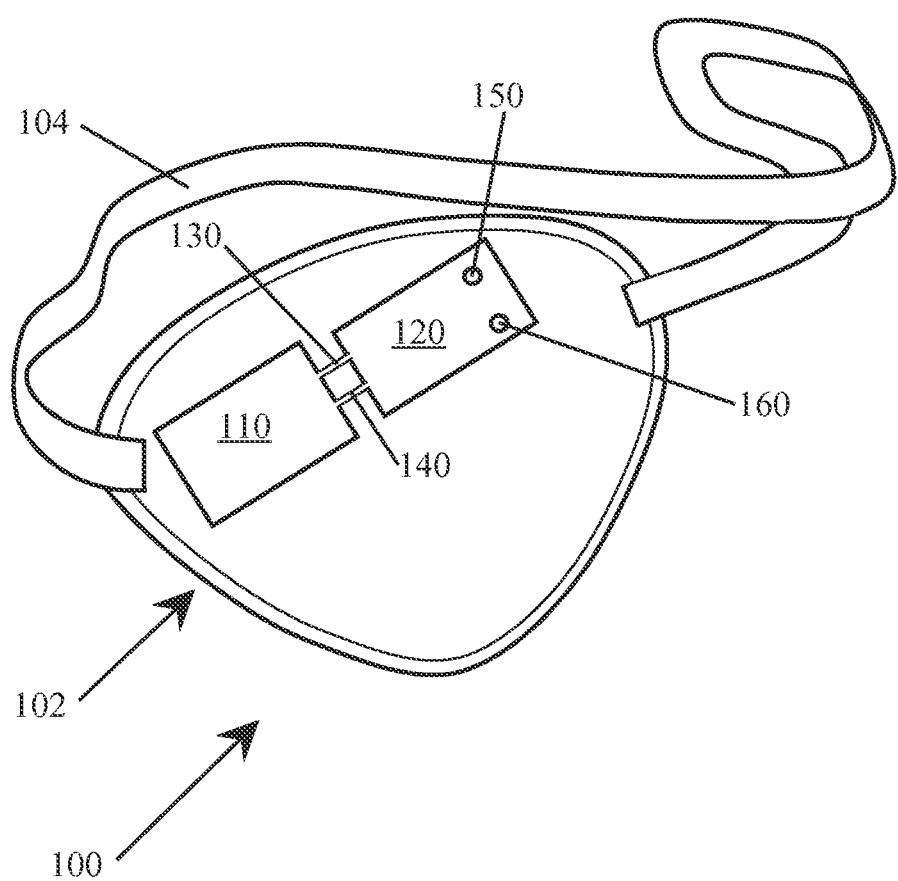
FIG. 1A illustrates a first embodiment of Applicants' ophthalmological device.
Figure 1B:
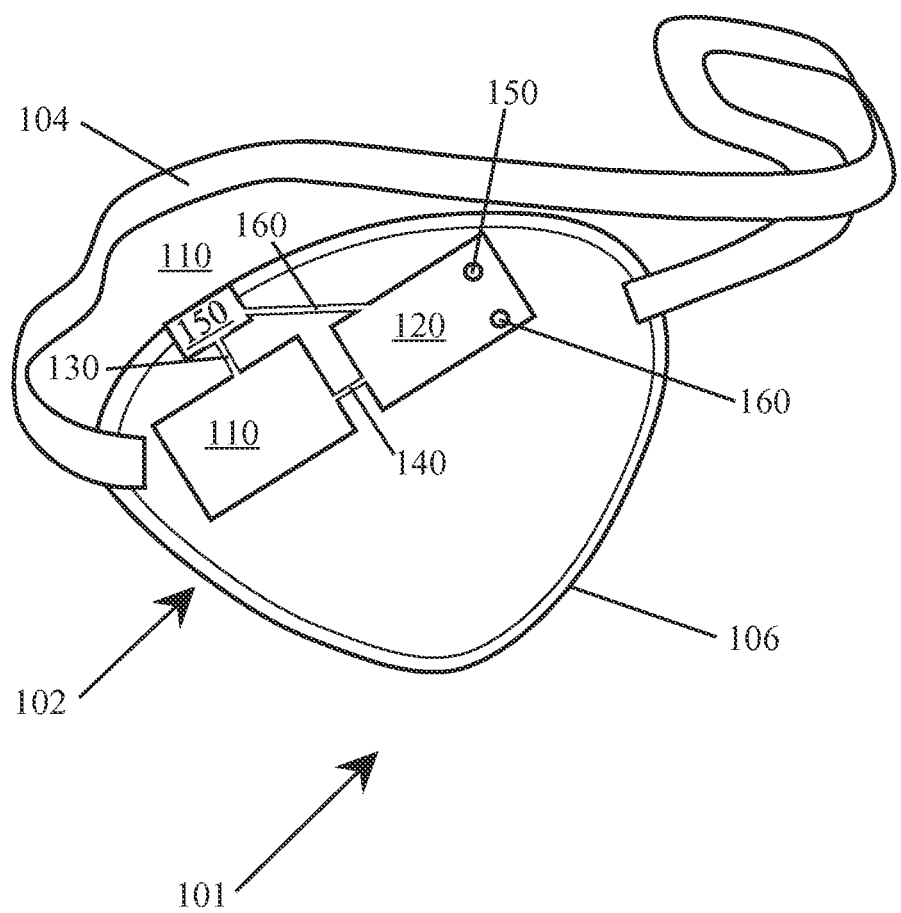
FIG. 1B illustrates a second embodiment of Applicants' ophthalmological device.
Figure 1C:
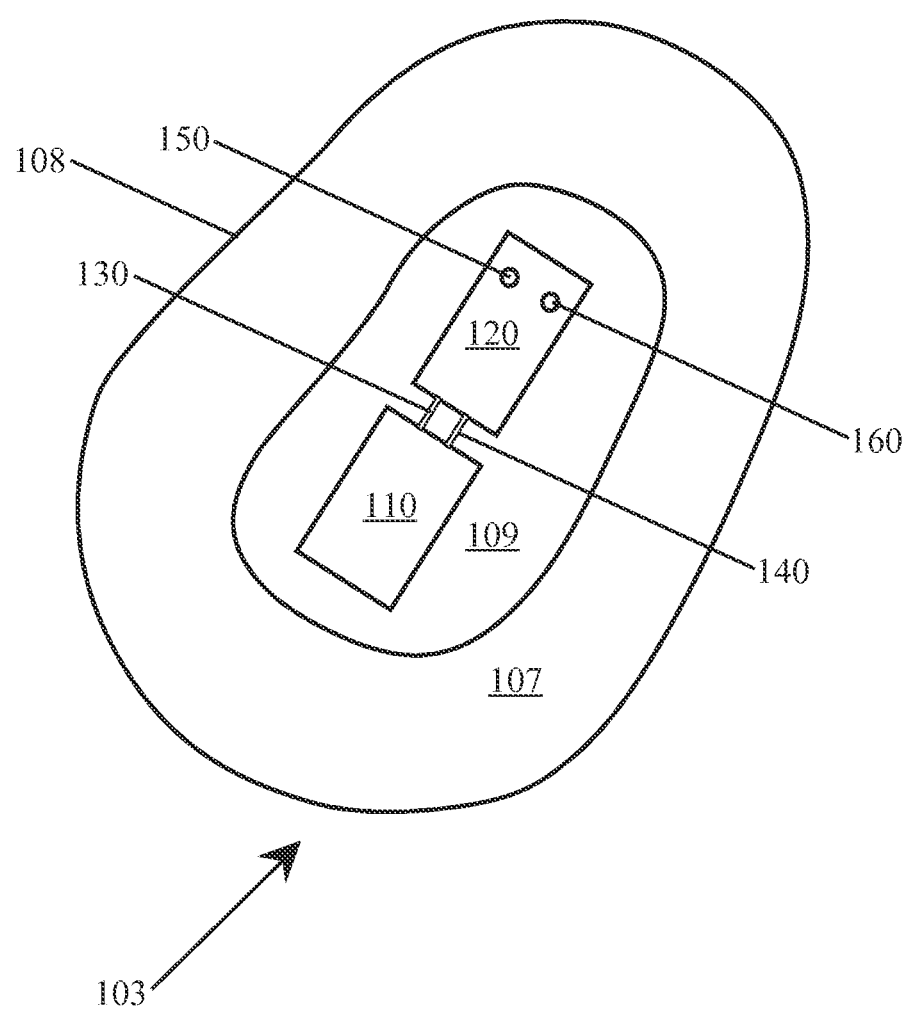
FIG. 1C illustrates a third embodiment of Applicants' ophthalmological device.
Figure 1D:
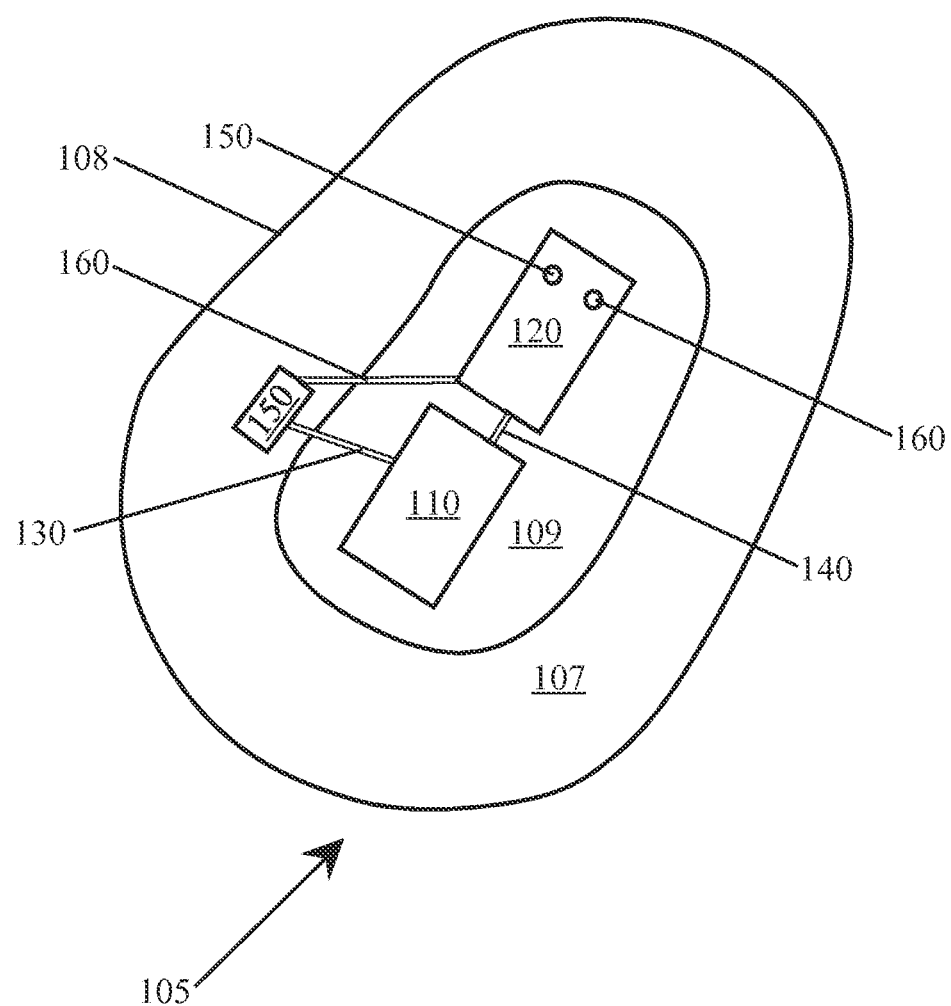
FIG. 1D illustrates a fourth embodiment of Applicants' ophthalmological device.

In the illustrated embodiments of FIGS. 1B and 1D, Applicants' ophthalmological device comprises an eye patch, a battery, a photodiode, and a thermistor, all disposed on an outer surface of the eye patch. In both embodiments, prior to the patient donning the ophthalmological device, the battery comprises a fully-discharged electrical potential. The photodiode continuously charges the battery as long as the photodiode is exposed to ambient light, either indoor lighting or sunlight. After the patient removes the ophthalmological device, Applicants' method measures the battery potential. Thereafter, Applicants' analysis module determines and stores a length of time that the patient wore Applicants' ophthalmological device that day. The procedure is repeated daily.

Figure 2A:
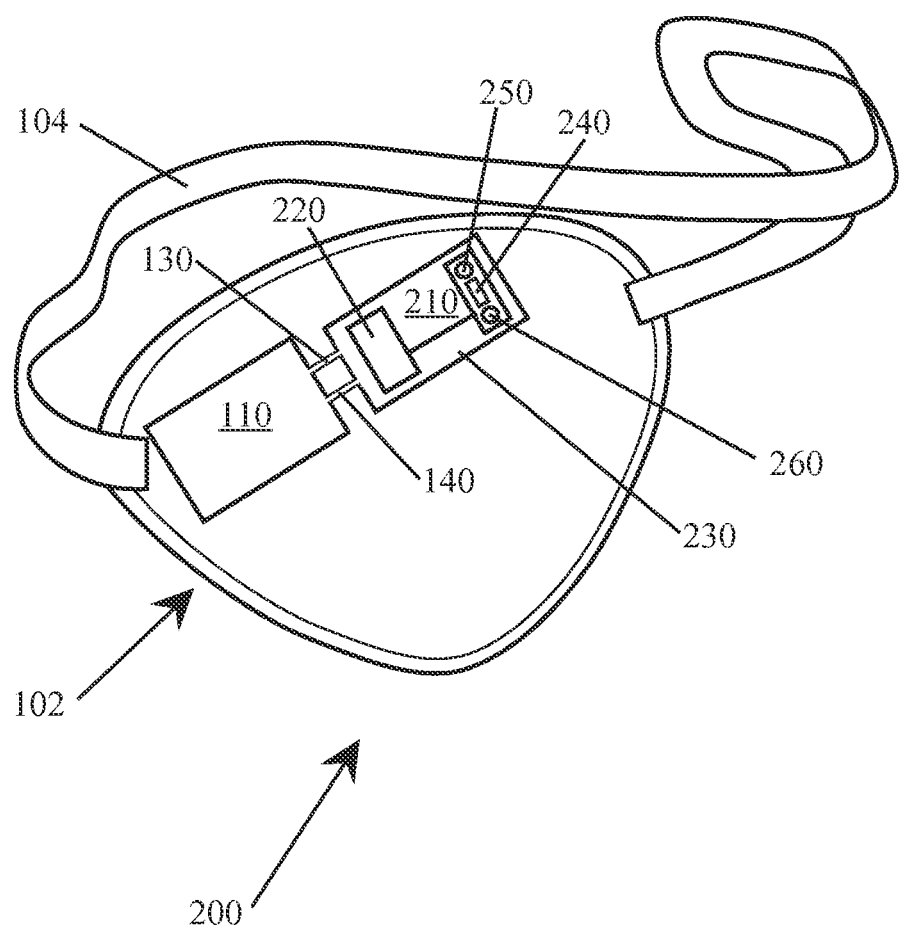
FIG. 2A illustrates a fifth embodiment of Applicants' ophthalmological device.
Figure 2B:
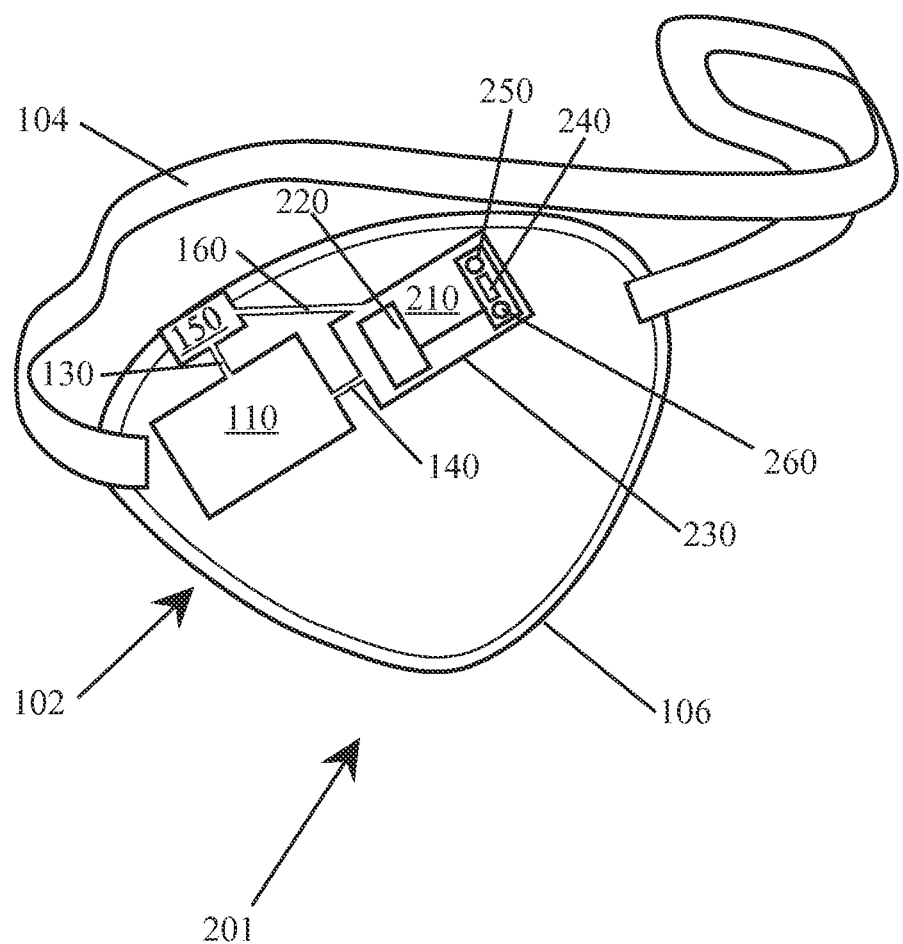
FIG. 2B illustrates a sixth embodiment of Applicants' ophthalmological device.
Figure 2C:
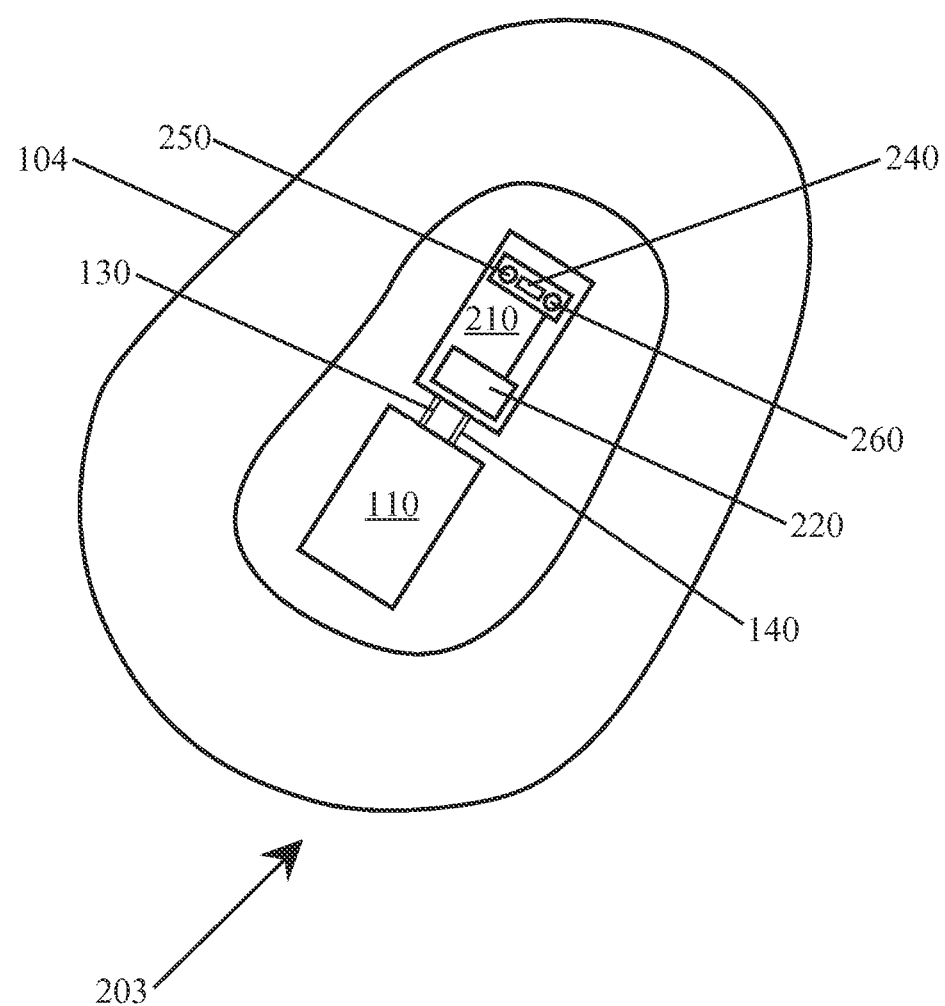
FIG. 2C illustrates a seventh embodiment of Applicants' ophthalmological device.

In the illustrated embodiments of FIGS. 2A and 2C, Applicants' ophthalmological device 200 comprises a photodiode and an oscillator comprising a counter. In the illustrated embodiments of FIGS. 2B and 2D, Applicants' ophthalmological device 201 comprises a photodiode, an oscillator comprising a counter, and a thermistor. The photodiode continuously supplies electrical current to the oscillator as long as the photodiode is exposed to ambient light, either indoor lighting or sunlight. After the patient removes the ophthalmological device, Applicants' method measures a value for the counter. Thereafter, Applicants' analysis module determines and stores the counter value and calculates a length of time that the patient wore Applicants' ophthalmological device that day. The procedure is repeated daily.

Referring now to FIG. 1A, Applicants' ophthalmological device 100 comprises eye patch 102, elastic strap 104, photovoltaic 110, and battery 120. Elastic strap 104 can be removeably disposed around a patient's head such that eye patch 102 covers an eye. Eye patch 102 comprises a substantially conical shape and comprises an outer surface and an inner surface. Photovoltaic 110 and battery 120 are disposed on the outer surface.

In certain embodiments, Applicants' ophthalmological device 100 would be sold in bulk, wherein a plurality of ophthalmological devices are sold in, and thereafter stored when not is use, in a light-proof container, such as for example and without limitation a cardboard box having a top lid.

When a particular ophthalmological device 100 is removed from the light-proof container and placed onto a patient, photovoltaic 110 is exposed to ambient light. In certain embodiments, a light-proof covering, such as for example a piece of electrical tape, is disposed over photovoltaic 103. When an ophthalmological device 100 is removed from a box containing a plurality of patches, the small piece of electrical tape is removed from photovoltaic 103, thereby exposing photovoltaic 103 to ambient light.

By "photovoltaic," Applicants mean the unbiased operating mode of a photodiode in which current through the device is entirely due to the transduced light energy. Photovoltaic 110 produces direct current electricity from ambient light, and that DC power is provided via one or more of power conduits 130/140 to recharge battery 120. In certain embodiments, photovoltaic assembly 320 comprises one or more photodiodes comprising thin film CdTe, CIGS, amorphous Si, microcrystalline Si, and the like.

Referring to FIG. 1C, Applicants' ophthalmological device 103 comprises an ORTOPAD 108, photovoltaic 110, and battery 120. ORTOPAD 108 comprises an oval shape which includes a peripheral portion 107 and a central portion 109. Portions 107 and 109 comprise a monostretch non-woven material. Peripheral portion 107 further comprises a non-allergenic latex-free adhesive on a first side. Central portion 109 further comprises a light protection inlay assuring that a covered eye is shielded from light.

In certain embodiments, Applicants' ophthalmological device 103 would be sold in bulk, wherein a plurality of ophthalmological devices are sold in, and thereafter stored when not is use, in a light-proof container, such as for example and without limitation a cardboard box having a top lid.

When a particular ophthalmological device 103 is removed from the light-proof container and placed onto a patient, photovoltaic 110 is exposed to ambient light. In certain embodiments, a light-proof coverings, such as for example a piece of electrical tape, is disposed over photovoltaic 103. When an ophthalmological device 103 is removed from a box containing a plurality of patches, the small piece of electrical tape is removed from photovoltaic 103, thereby exposing photovoltaic 103 to ambient light.

Figure 5A:
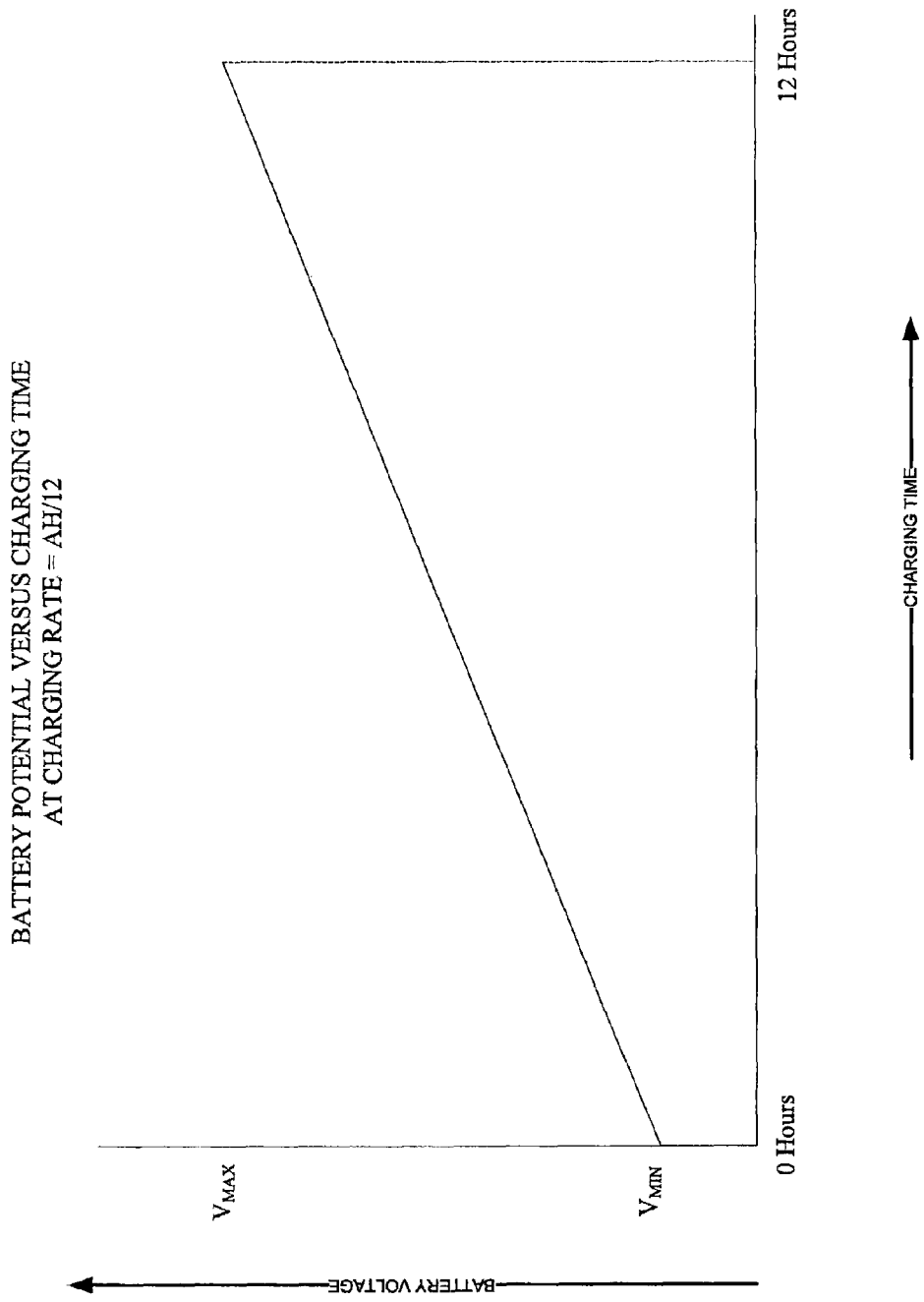
FIG. 5A graphically illustrates a battery potential versus charging time at a charging rate equal to AH/12.

Referring now to FIG. 5A, battery 120 comprises a $V_{MIN}$, comprising a voltage potential when the battery is completely discharged, and a $V_{MAX}$, comprising a voltage potential when the battery is maximally charged. For example, a battery comprising a $V_{MAX}$ of 2 volts may comprise, for example and without limitation, a $V_{MIN}$ of about 1.6 volts. Curve 510 graphically illustrates the voltage potential of battery 120 as a function of time, wherein battery 120 comprises a nominal amperage/hour ("AH") discharge capability, and wherein battery 120 is charged using a charge current of AH/12. As illustrated in FIG. 5A, the voltage potential increases substantially linearly from voltage $V_{MIN}$ at time $T_0$ to a voltage potential of $V_{MAX}$ at time $T_{12\ HOURS}$.

In certain embodiments, photovoltaic assembly 110 comprises a charge limiter that provides charging energy to battery 120 comprising a voltage $V_{MAX}$ at a charge current equal to AH/12. Referring now to FIGS. 1A and 5B, prior to removing ophthalmological device 100 from its light-proof container, battery 120 comprises a voltage $V_{MIN}$. For example, in certain embodiments, battery 120 comprises a $V_{MIN}$ of about 1.6 volts and a $V_{MAX}$ of about 2 volts. Upon placing ophthalmological device 100 onto a patient, and optionally removing a light blocking material from the photovoltaic 110, photovoltaic 110 is then exposed to ambient light and begins to charge battery 120 at a voltage $V_{MAX}$ and a charge current of AH/12.

When ophthalmological device is removed from the patient, the voltage of battery 120 can be measured using a volt meter interconnected to battery terminals 150 and 160. For example and referring to FIG. 5B, if a voltage $V_{ACTUAL}$ is measured after removing ophthalmological device from a patient, then using charging curve 510, a time $T_{WORN}$ comprising a time interval during the patient actually wore ophthalmological device 100 can be determined. As those skilled in the art will appreciate, the value of $T_{WORN}$ can be calculated using equation (i):

$$V_{ACTUAL} = (m)(T_{WORN}) + V_{MIN} \tag{i}$$

wherein (m) is the slope of charging curve 510.

Referring now to FIGS. 1B and 1D, Applicants' ophthalmological devices 101 and 105 comprise either an eye patch 102 and elastic strap 104, or an ORTOPAD 108, respectively, in combination with photovoltaic 110, battery 120, and thermistor 150. In ophthalmological device 103, thermistor 150 is disposed on periphery 106 of eye patch 102. In ophthalmological device 105, thermistor 150 is disposed on peripheral portion 107 of ORTOPAD 108. Photovoltaic 110 provides electrical energy to battery 120 via thermistor 150.

As those skilled in the art will appreciate, a thermistor comprises a resistor wherein the resistance varies as a function of temperature. Thermistor 150 comprises a Negative Temperature Coefficient, wherein the resistance of thermistor 150 decreases with temperature. When a patient is thermally equilibrated in a room temperature environment, the surface temperature of that patient's skin is about 33° C. or 91° F.

In certain embodiments, thermistor 150 comprises a high resistance at temperatures less than about 86° F., such that no charging current flows to battery 120. By "high resistance, Applicants mean a resistance of at least 3 kilo ohms. At temperatures greater than about 86° F., thermistor 150 comprises minimal resistance, such that if photovoltaic 110 is exposed to ambient light, electrical energy comprising a voltage $V_{MAX}$ at a current of AH/12 is provided to battery 120 via power conduit 130, thermistor 150, and power conduit 160. By "minimal resistance," Applicants mean about 30 ohms.

Ophthalmological device 101 is worn such that eye patch 102 covers a patient's "strong eye," and such that thermistor 150 is in contact with the surface of the patient's skin. When a patient wears ophthalmological device 101, photovoltaic 110 is exposed to ambient light, thermistor 150 is heated by the patient's skin to a temperature of about 90° F., battery 120 receives electrical energy comprising a voltage $V_{MAX}$ at a current of AH/12. When the patient removes ophthalmological device 101, thermistor 150 cools to a temperature less than 86° F., and even if photovoltaic is exposed to ambient light, no charging current is provided to battery 120.

In order to mitigate the effects of a patient leaving a warm environment and entering a cold environment, such as for example and without limitation leaving a heated building in the winter season, where even though the patient still wears Applicants' ophthalmological device, and even though thermistor 150 remains in contact with the patient's skin, the ambient temperature could be low enough to cause the temperature of thermistor 150 to fall below about 86° F., in certain embodiments thermistor 150 must remain at a temperature less than about 86° F. for more than about 10 minutes for charging current to be discontinued to battery 120. In certain embodiments, thermistor 150 is encapsulated with a thermally insulating material. In certain embodiments, thermistor assembly 150 comprises a temperature sensor, a timing device comprising a processor, microcode encoded in the timing device, and a switch interconnected between the battery and the photovoltaic. In these embodiments, if the temperature sensor measures a temperature less than about 86° F. the microcode initiates the timing device. If the temperature sensor continuously measures a temperature less than about 86° F. for a designated time interval encoded in the microcode, then the processor places the switch in an "off" state such that no charging current is provided to battery 120.

In certain embodiments, the designated time interval is about 5 minutes. In certain embodiments, the designated time interval is about 10 minutes. In certain embodiments, the designated time interval is about 15 minutes. In certain embodiments, the designated time interval is about 30 minutes.

Figure 3A:
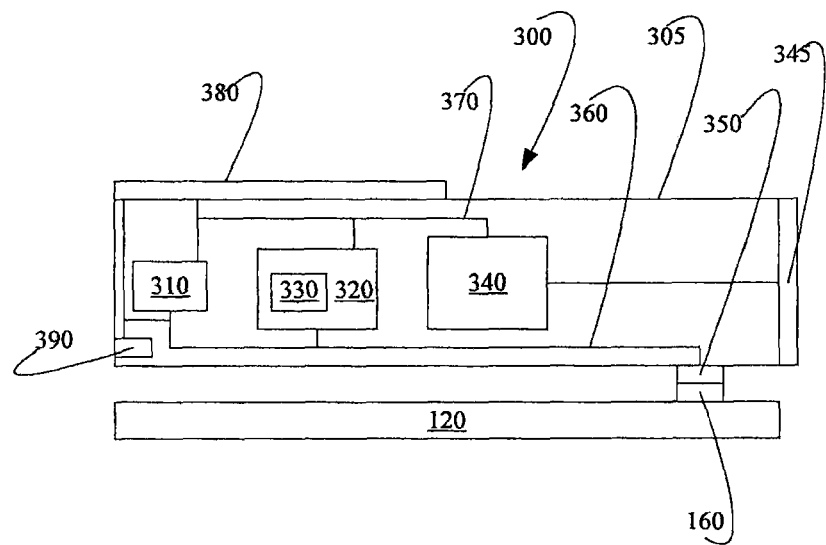
FIG. 3A is a block diagram showing a first embodiment of Applicants' analysis module.
Figure 3B:
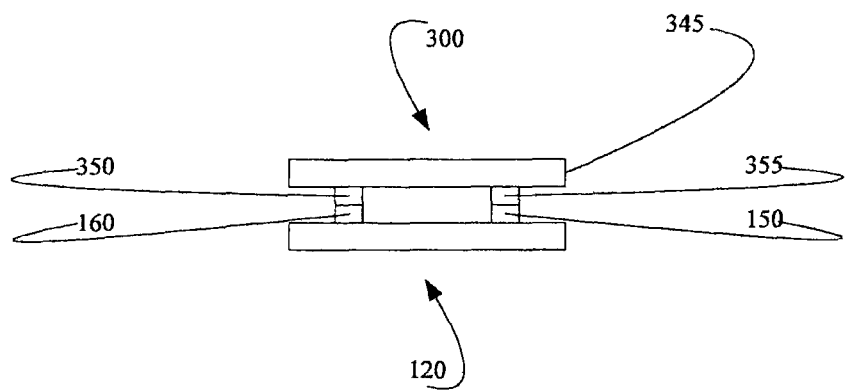
FIG. 3B shows the analysis module of FIG. 3A in communication with either the ophthalmological device of either FIG. 1A or FIG. 1B.

Referring now to FIGS. 3A and 3B, Applicants' hand-held analysis module 300 can be releasably coupled to battery 120, determine the voltage potential of battery 120, store that voltage potential in a database, and discharge battery 120 to a voltage potential equal to $V_{MIN}$. In the illustrated embodiment of FIG. 3A, hand-held analysis module 300 comprises housing 305, processor 310, computer readable medium 320, database 330 encoded in computer readable medium 320, battery 340, battery recharging coupling 345, data input port 350, input port 355, touch screen 380, and data output port 390. Processor 310, computer readable medium 320, data input port 350, touch screen 380, and data output port 390, are interconnected to communication bus 360. Processor 310, computer readable medium 320, battery recharging coupling 345, and touch screen 380, are interconnected to power bus 370.

When input ports 350 and 355 are interconnected to battery terminals 150 and 160 as shown in FIG. 3B, analysis module 300 can measure the voltage potential of battery 120. In certain embodiments, a measured voltage potential is encoded in database 330. In certain embodiments, a measured voltage potential, in combination with a date stamp comprising the time and date the measurement is made, are encoded in database 330. In certain embodiments, processor 310 determines a $T_{WORN}$ using Equation (i), and encodes that $T_{WORN}$ value in database 330. In certain embodiments, processor 310 determines and encodes in database 330 a $T_{WORN}$ value and an associated time stamp comprising the time and date the voltage measurement was made.

Referring now to FIGS. 2A and 2C, Applicants' ophthalmological devices 200 and 203 comprise either eye patch 10 and elastic strap 104, or ORTOPAD 108, respectively, in combination with photovoltaic 110, oscillator 220, memory device 230, and counter value 240 encoded in memory device 230.

In certain embodiments, memory device 230 is integral with oscillator 220. In certain embodiments, memory device 230 comprises non-volatile memory. In certain embodiments, memory device 230 comprises, for example and without limitation, a magnetic information storage medium, an optical information storage medium, an electronic information storage medium, and the like. By "electronic information storage medium," Applicant mean, for example and without limitation, a PROM, EPROM. EEPROM, Flash PROM, compactflash, smartmedia, and the like.

In certain embodiments, Applicants' ophthalmological device 200/203 would be sold in bulk, wherein a plurality of ophthalmological devices are sold in, and thereafter stored when not is use, in a light-proof container, such as for example and without limitation a cardboard box having a top lid.

When a particular ophthalmological device is removed from the light-proof container and placed onto a patient, photovoltaic 110 is exposed to ambient light. In certain embodiments, a light-proof covering, such as for example a piece of electrical tape, is disposed over photovoltaic 103. When an ophthalmological device is removed from a box containing a plurality of patches, the small piece of electrical tape is removed from photovoltaic 103, thereby exposing photovoltaic 103 to ambient light.

Figure 2D:
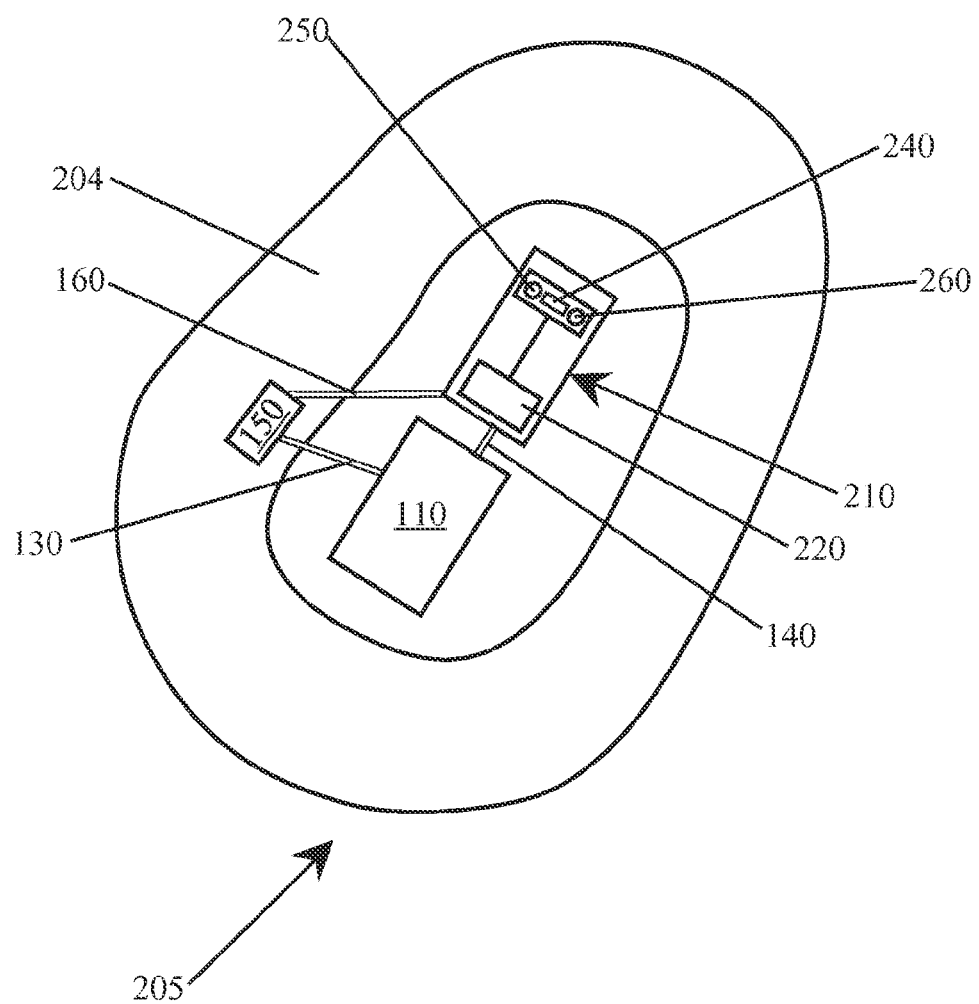
FIG. 2D illustrates an eighth embodiment of Applicants' ophthalmological device.

Referring now to FIGS. 2B and 2D, Applicants' ophthalmological device 201/205 comprises either an eye patch 102 and elastic strap 104, or an ORTOPAD 108, respectively, in combination with photovoltaic 110, oscillator 220, memory device 230, counter value 240, in addition to comprising thermistor 150 disposed on periphery 106 of eye patch 201. Photovoltaic 110 provides electrical energy to oscillator 220 via thermistor 150.

Figure 4A:
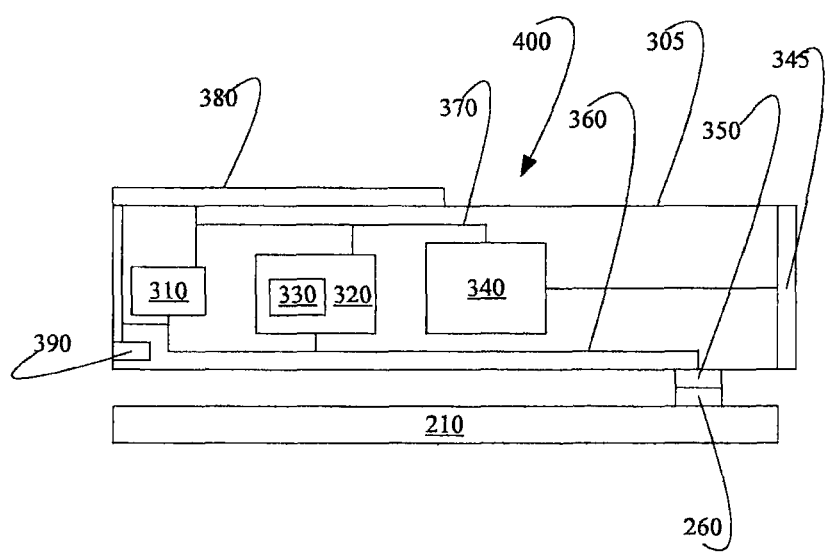
FIG. 4A is a block diagram showing a second embodiment of Applicants' analysis module.
Figure 4B:
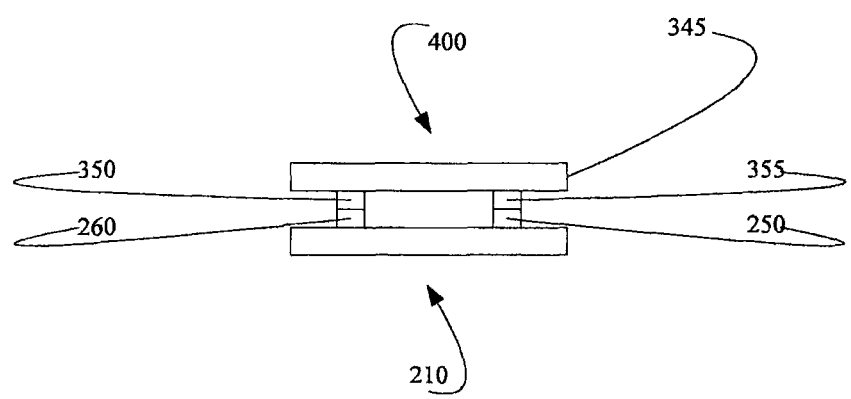
FIG. 4B shows the analysis module of FIG. 3A in communication with either the ophthalmological device of either FIG. 2A or FIG. 2B.

Referring now to FIGS. 4A and 4B, Applicants' hand-held analysis module 400 can be releasably coupled to oscillator/memory assembly 210, determine a count value 240, store that count value in a database, and reset count value 240 to zero. In the illustrated embodiment of FIG. 4A, hand-held analysis module 400 comprises housing 305, processor 310, computer readable medium 320, database 330 encoded in computer readable medium 320, battery 340, battery recharging coupling 345, data input port 350, input port 355, touch screen 380, and data output port 390. Processor 310, computer readable medium 320, data input port 350, touch screen 380, and data output port 390, are interconnected to communication bus 360. Processor 310, computer readable medium 320, battery recharging coupling 345, and touch screen 380, are interconnected to power bus 370.

When input ports 350 and 355 are interconnected to data ports 250 and 260 as shown in FIG. 4B, analysis module 400 can download counter value 240. In certain embodiments, a measured counter value 240 is encoded in database 330. In certain embodiments, a measured counter value 240, in combination with a date stamp comprising the time and date the download is made, are encoded in database 330. In certain embodiments, processor 310 determines a $T_{WORN}$ using the downloaded counter value 240 encoded in database 330. In certain embodiments, processor 310 determines and encodes in database 330 a $T_{WORN}$ value and an associated time stamp comprising the time and date the counter value 240 was downloaded. In certain embodiments, the calculated $T_{WORN}$ is displayed on touch screen 380.

Regardless of the internal architecture of Applicants' ophthalmological device, when the patient returns to the physician's office with either analysis module 300 or analysis module 400, the ophthalmologist can obtain the calculated $T_{WORN}$ values, an average $T_{WORN}$ value, and the aggregate time that one or more eye patches were exposed to ambient light during the therapeutic period.

In certain embodiments, the calculated $T_{WORN}$ values, an average TWORN value, and the aggregate time that one or more eye patches were exposed to ambient light during the therapeutic period, can be displayed on touch screen 380, and that data can be manually recorded. In certain embodiments, the calculated $T_{WORN}$ values, an average TWORN value, and the aggregate time that one or more eye patches were exposed to ambient light during the therapeutic period, can be downloaded from database 330 using data port 390.

In certain embodiments, data port 390 comprises a USB 1.1 port. In certain embodiments, data port 390 comprises a USB 2.0 port. In certain embodiments, data port 390 comprises a USB 3.0 port. In certain embodiments, data port 390 comprises an IEEE 1394 Standard port, i.e. a firewire port.

Regardless of the architecture of data port 390, Applicants' analysis module 300/400 can be interconnected to a computer device via data port 390, and a calculated $T_{WORN}$ values, an average TWORN value, and an aggregate time that one or more eye patches were exposed to ambient light during the therapeutic period, can be downloaded from database 330, via data port 390, and uploaded to the external computing device for storage and analysis.

While the preferred embodiments of the present invention have been illustrated in detail, it should be apparent that modifications and adaptations to those embodiments may occur to one skilled in the art without departing from the scope of the present invention as set forth in the following claims.

I claim:

1. An ophthalmological device, comprising:
   an eye patch;
   a photovoltaic; and
   a battery, wherein said photovoltaic is interconnected to said battery
   a switch interconnected between said photovoltaic and said battery;
   a temperature sensor;
   a timing device comprising a processor;
   microcode encoded in the timing device;
   wherein if the temperature sensor continuously measures a temperature less than about 86° F. for a designated time interval encoded in the microcode, then the processor disposed the switch in an off state such that no charging current is provided to the battery.

2. The ophthalmological device of claim 1, wherein:
   said photovoltaic comprises a charge limiter; and
   said photovoltaic is configured to charge said battery.

3. The ophthalmological device of claim 2, wherein:
   said battery comprises a nominal amperage/hour ("AH") discharge capability; and
   said photovoltaic is configured to provide charging energy to said battery at a charge current of AH/12.

4. The ophthalmological device of claim 3, wherein said thermistor comprises a high resistance at temperatures less than about 86° F.

5. The ophthalmological device of claim 4, wherein said thermistor comprises a resistance of about 3 kilo ohms at temperatures less than about 86° F.

6. The ophthalmological device of claim 4, wherein said thermistor comprises a minimal resistance at temperatures greater than about 86° F.

7. The ophthalmological device of claim 6, wherein said thermistor comprises a resistance of about 30 ohms at temperatures greater than about 86° F.

8. The ophthalmological device of claim 1, wherein said eye patch comprises periphery, further comprising a thermistor disposed on said periphery, wherein said thermistor is interconnected to said photovoltaic and to said battery.

9. The ophthalmological device of claim 1, wherein said designated time interval is about 5 minutes.

* * * * *